| United States Patent [19] | [11] Patent Number: 4,812,159 |
| Freepons | [45] Date of Patent: Mar. 14, 1989 |

[54] PLANT GROWTH REGULATORS DERIVED FROM CHITIN

[76] Inventor: Donald E. Freepons, 535 N. Montana, Kennewick, Wash. 99336

[21] Appl. No.: 25,586

[22] Filed: Mar. 13, 1987

Related U.S. Application Data

[63] Continuation-in-part of Ser. No. 846,064, Mar. 31, 1986, abandoned.

[51] Int. Cl.$^4$ ............................ C05F 1/00; C05G 3/00
[52] U.S. Cl. ............................................ 71/16; 71/27; 71/77; 47/57.6
[58] Field of Search ..................... 71/1, 11, 16, 27, 77; 47/57.6

[56] References Cited

U.S. PATENT DOCUMENTS 1,199,496  4/1908  Peniston et al.
4,031,025  6/1977  Vanlerberghe et al. ....... 210/698 X
4,539,038  9/1985  Gombert.
4,562,663  1/1986  Redenbaugh.

OTHER PUBLICATIONS

Stoessel and Leuba, Phytopath. Z., 111, 1984, pp. 82–84, "Effect of Chitosan, Chitin and some Aminosugars on Growth of Various Soilborne Phytopathogenic Fungi".
Hirano et al, CA 102(21), 183724f, "Several Novel . . . Chitosan", 1984.
Albersheim et al., *Scientific American*, Sep. 1985 (pp. 63–64).
Agricultural Biotechnology News, Jan./Feb. 1987, p. 11.

*Primary Examiner*—Ferris H. Lander
*Attorney, Agent, or Firm*—Robbins & Laramie

[57] ABSTRACT

A plant growth regulating composition comprising chitosan and a non-phytotoxic acid in the form of an aqueous solution or a blend of dry powders. The composition may be applied to the soil in which seeds are to be planted, the seeds themselves, or the foilage of an emerging plant.

43 Claims, No Drawings

PLANT GROWTH REGULATORS DERIVED FROM CHITIN

CROSS-REFERENCE TO RELATED APPLICATION

This application is a continuation-in-part of application Ser. No. 846,064, filed on Mar. 31, 1986 and now abandoned.

BACKGROUND OF THE INVENTION

1. Field of the Invention

The invention pertains to plant growth regulators and processes for their use. Plant growth regulators are substances which are used to influence the growth characteristics of plants. The growth characteristics influenced include growth rate, number of tillers produced per plant, standability of the plant, root stimulation and germination enhancement.

The plant growth regulators of the present invention are comprised of chitosan, which is a derivative of chitan. Chitin is a polysaccharide consisting predominantly, if not entirely, of unbroken chains of $\beta$-(1-4)-linked 2-acetamido-2-deoxy-D-glucose (N-acetyl-D-glucosamine) residues. It can thus be regarded as a derivative of cellulose, in which the C-2 hydroxyl groups have been replaced by acetamido residues. It is found in huge quantities in the natural environment. Estimates of yearly production exceed several billions of tons. It is the structural material of all exoskeletal animals; of all members of arthropoda (crustacea, insects, spiders, etc.), mollusca (snails, squids, etc.), coelenterata (marine organisms such as hydoids and jellyfish) and nematoda (unsegmented worms). Chitin is also found in various fungi.

In crustacea, the shell comprises a matrix of protein chemically combined with chitin which is mixed with calcium carbonate. In order to free the chitin from the protein, the shell of the crustacean is treated with an alkaline aqueous solution which penetrates the interstices of the shell matrix to rupture the bond between the protein and chitin. To then separate the chitin from the calcium carbonate, the residue from the protein separation is treated with an acid to remove the calcium carbonate and leave substantially pure chitin. The acid used is preferably hydrochloric acid.

The demineralized chitin is washed on a rotary vacuum filter and dried in a rotary hot-air dryer. At this point, the chitin can be converted directly to one of its derivatives, chitosan. Chitin is a less reactive compound than the related compound, cellulose, and because of this property, it has been little used by industry. Some uses include as a dry hair shampoo, a flocculant, and a matrix for photo processing and for some enzymes.

2. Description of the Prior Art

Chitin has also been used as an adhesive, as disclosed by Rigby in U.S. Pat. No. 2,047,226, as a sizing agent for paper, as disclosed by Merrill in U.S. Pat. No. 2,047,218, as an emulsifier, as disclosed by Rigby in U.S. Pat. No. 2,047,225, and as filaments, threads, fibers, tubes, straws and seamless sausage casings, as disclosed by Thor in U.S. Pat. No. 2,217,823.

Muzzarelli, in Chitin, Pergamon Press (1977), at pages 207-254, has described industrial uses of chitin including the removal of certain radioisotopes from water by percolation, the removal of mercury and copper from water, as a textile finish, in polymeric dyes, as a soil repellant, as a shrinkproofing for wool, in photographic products and processes, and in dewatering municipal sludge. At pages 255-265, Muzzarelli describes medical uses of chitin including artificial kidney membranes, preparations for immunization against parasites, biodegradable pharmaceutical carriers, blood anticoagulants, aggregation of leukemia cells, wound healing accelerators and microbiologic media.

Additionally, chitin has been used to form a gel for encapsulating somatic embryos, zygotic embryos or meristematic tissue of plants, as described by Redenbaughin U.S. Pat. No. 4,562,663. The use of Redenbaugh of chitin as an encapsulating medium is unrelaetd to any plant growth regulation function. As explained by Redenbaugh, the encapsulation medium "must allow the meristem or embryo respiration by permitting diffusion of gases". The encapsulation medium should also "provide an environment strong enough to resist external abrasion and adverse forces, yet pliable enough to allow the growth of the embryo and its germination at the appropriate time".

Use of chitin as plant fertilizer has been disclosed by Peniston et al. in U.S. Pat. No. 4,199,496. Although the Peniston et al. patent is concerned with processes for the recovery of chemicals from the shells of crustacea, the use of chitin as a fertilizer is mentioned because chitin is one of the chemicals recovered from the shells of crustacea. As explained by Peniston et al., "chitin can be used as a fertilizer to release nitrogen, slowly, into the soil and thereby over a relatively long period of time increase the nitrogen content of the soil".

However, fertilizers differ from plant growth regulators. A fertilizer is any material which is added to soil to supply chemical elements needed for plant nutrition. Most commonly, fertilizers are designated by a three-digit number which represents the respective amounts of nitrogen, phosphorus and potassium. A plant growth regulator, on the other hand, is an organic compound which will inhibit, accelerate or in some way influence physiological processes in plants. Where a fertilizer merely supplies needed elements for a plant to grow in its normal fashion, a plant growth regulator causes some sort of change in the plant's normal growth pattern. Some of the influences of plant growth regulators include germination enhancement, root stimulation, plant stature control, shortening or lengthening of the time to maturity of the plant, ripening control, increased yield, fruit and vegetable color control, and shortened or lengthened dormancy. Some known plant growth regulators are cytokinins and gibberellic acids.

At present, there are no known materials which have the ability to influence, affect, enhance or increase the reproductive sites, e.g., tillers, pods, ears, etc., of plants. There are also no known derivatives, compositions or combinations of chitin used as plant growth regulators.

SUMMARY OF THE INVENTION

In one embodiment, the invention is a process for influencing plant growth comprising the distribution of an aqueous solution of deacetylated chitin (chitosan, as more fully defined below) in a non-phytotoxic acid in the soil in which plants are to be grown. The aqueous solution comprises about 0.1% by volume to about 10% by volume of deacetylated chitin and about 0.1% by weight to about 10% by weight of the non-phytotoxic acid. The remainder of the solution is comprised of water. When distributed, the aqueous solution is applied in the seed planting zone of a plant. The non-phytotoxic acid is preferably glutamic acid.

In another embodiment of the invention, the aqueous solution of deacetylated chitin and non-phytotoxic acid is applied directly to the plant seeds. Application of the solution to the seeds is generally performed either by metered spraying or soaking.

Further embodiments of the invention comprise distributing a blend of powdered deacetylated chitin and powdered non-phytotoxic acid into the seed planting zone in soil or applying the powdered blend directly onto the seeds. Anotehr embodiment of the invention comprises applying an evaporated and ground solution of chitosan in glutamic acid to the seed planting zone of soil or to the seeds themselves.

When the inventive processes are followed, the tillerability of various cereal grains is enhanced. The processes can also be expected to influence other areas of plant growth, such as roots, stems, leaves, blossoms, internal structures and any seed holding structure such as tillers, pods, ears, etc. Treatment applications of the aqueous solution can be made to the soil, the seeds or the foliage of emerging plants.

In its application as a plant growth regulator, it is unknown what precise biochemical action takes place, but Dr. Lee A. Hadwiger at Washington State University, Pullman, Wash., suggests an interaction of the deacetylated chitin with the immune system of the plant. It is also possible that chitosan acts as an antagonist and/or protagonist to and with the gibberellic acids to influence plant development dynamics. It has also been theorized that chitosan's metabolic pathway includes the formation of certain oligosaccharins that regulate enzymatic-specific growth processes.

DETAILED DESCRIPTION OF THE INVENTION

Deacetylated chitin, in combination with a non-phytotoxic acid such as an amino acid, has been found to be a particularly effective plant growth regulator. Plant growth regulators cause a change in a plant's normal growth pattern. Some specific examples of plant growth regulators are germination enhancers, root stimulants, plant stature controllers, plant maturity agents, ripening agents and plant dormancy agents. Germination enhancers cause rapid emergence of the plant from the seed, and thereby allow better weed control around the plant. Root stimulants cause quicker and more secure plant establishment in the soil. Plant stature controllers cause stronger stems to develop so that the plant can better withstand strong winds and other meterological conditions. Agents that shorten the time to maturity of a plant allow for timely harvesting of the plant before foul weather. Ripening agents are used to provide an even ripening of a whole field of plants in order to allow timely harvesting. Ripening agents are very often used on pineapples, sugar cane, oranges, tomatoes and apples. Agents that shorten or lengthen the dormancy of crops help to prevent sprouting and the subsequent degrading of the produce which renders it unfit for human consumption. Agents that lengthen dormancy are often used with crops such as onions and potatoes.

Although fertilizers can also cause increased yield from plants, they do so at a cost. High rates of fertilizer application increase plant yield potential by creating larger plants, but such unusually large plants are susceptible to delayed maturity and to a condition known as lodging. Lodging occurs when a plant is too tall and/or too heavy to support itself and is therefore easily affected by winds which cause the plant to tip and fall and lay on the ground surface. In such a lodged condition, plants are difficult to harvest because of their close proximity to the soil surface, thus resulting in reduction of crop yield. Seed damage is also likely with lodged plants because of their contact with damp soil, and with pests such as rodents and insects which contaminate the crop and render it unmarketable.

With rice, high rates of nitrogen application will often cause kernel sterility or "blanking", i.e., the plant flower will not pollenate (causing a "skipped" kernel). Blanking results when a kernel is not pollenated and all that remains is a husk. Additionally, with unusually high rates of nitrogen application, rice yields have been reduced by as much as 30%. High rates of fertilizer application have quite often delayed rice plant maturity past harvesting time and into foul weather periods, thereby resulting in reduced crop yields and sometimes in total crop loss. Plant growth regulators cause increased yields without the problems associated with fertilizers. An additional advantage of plant growth regulators comprised of chitin derivatives is the potentially limitless supply of chitin available.

Chitin is a mucopolysaccharide consisting predominantly of unbroken chains of $\beta$-(1-4)-linked 2-acetamido-2-deoxy-D-glucose (N-acetyl-D-glucosamine) residues of the formula

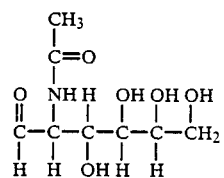

The deacetylated chitin, also known as chitosan, is obtained by reacting chitin with concentrated, aqueous potassium hydroxide at about 160° C. Chitosanis a polysaccharide consisting predominantely of unbroken chains of D-glucosamine residues of the formula:

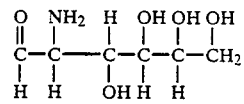

At present, chitin and chitosan should be thought of as being on a spectrum. At one end of the spectrum is a polysaccharide consisting of 100% acetylated-D-glycosamine members and at the opposite end of the spectrum is the polysaccharide consisting of 100% glucosamine members which are not acetylated. In theory, chitin and chitosan are the respective polysaccharides at each end of the spectrum described above. In reality, however, chitin and chitosan merely approach their respective ends of the spectrum. Chitin has far more acetylated-D-glucosamine members than non-acetylated members, while chitosan is predominantly composed of non-acetylated-D-glucosamine members (although some acetylated members are also present). Pure, i.e., 100% acetylated chitin is not found in nature, and a method for obtaining pure chitosan, i.e., 100% deacetylated chitin has not yet been developed.

Chitosan can be combined with a non-phytotoxic acid, preferably an amino acid, and most preferably glutamic acid, to yield a final product in the form of either an aqueous solution, a dry powder blend or a powder created by grinding the residue of an evaporated chitosan/glutamic acid solution. The formulation of the aqueous solution comprises about 0.1% by volume to about 10% by volume chitosan dissolved in about 0.1% by volume to about 10% by volume of the non-phytotoxic acid. A preferred formulation comprises about 2% by volume chitosan and about 2% by volume of the non-phytotoxic acid. The remainder of the solution is comprised of water.

The preparation of the dry powder blend requires the grinding of the chitosan into a powder with an average particle diameter of about 0.5 μm to about 100 μm. The non-phytotoxic acid must be similarly ground to produce particles with an average diameter of between about 0.5 μm and 100 μm. Dry, powdered chitosan is available from Protan Laboratories of Redmond, Wash., and dry, powdered glutamic acid is available from Ajinomoto U.S.A., Inc., of Los Angeles, Calif.. Commercially available chitosan contains less than 1% ash. A preferred average particle diameter for both the chitosan and the non-phytotoxic acid is between about 10 μm and about 30 μm. The chitosan and the non-phytotoxic acid are blended such that the weight ratio of chitosan to non-phytotoxic acid is between about 1:10 and about 10:1. The preferred weight ratio of chitosan to non-phototoxic acid is 1:1.

Manufacture of a powder from the evaporated residue of an aqueous solution comprises first preparing a concentrated aqueous solution of 3% by volume or greater chitosan and a non-phytotoxic acid. The non-phytotoxic acid is preferably present in the same volume percentage as the chitosan. The concentrated solution is evaporated, and the residue is ground until the average particle diameter is between about 10 μm and about 30 μm.

The preferred non-phytotoxic acid to be used in both the aqueous solution and the dry powder blend is glutamic acid. Glutamic acid has the following structural formula:

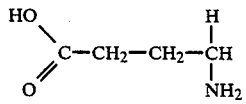

When used, the aqueous solution, dry powder blend or evaporated residue powder may be applied to plant seeds, to the soil in which the seed is to be planted, or to the foliage of an emerging plant. However, the solution, powder blend or evaporated residue powder is most commonly applied directly to the seeds or soil. When applied to seeds, the chitosan/glutamic acid solution should be applied about 60 hours prior to planting. In contrast, the dry powder blend or evaporated residue powder of chitosan and glutamic acid may be applied to seeds up to about six months prior to planting. Generally, the application of either the aqueous solution, the dry powder blend or evaporated residue powder in the seed planting zone takes place at the same time as the seed planting.

Application of the aqueous solution to the soil requires distribution of the solution in the seed planting zone of the plant. The seed planting zone is that area in close proximity to where the seed will be planted. Most commonly, the aqueous solution is applied at the same time that the seed is planted. The application rate of the aqueous solution is such that between approximately 10 and approximately 1,000 grams of chitosan are applied per acre of soil. A preferred rate of application results in the distribution of approximately 33 grams of chitosan per acre of soil.

The application of the dry powder blend in the seed planting zone of the soil is conducted in much the same manner as the application of the aqueous solution to the soil. Between about 10 grams and about 1,000 grams, and preferably about 30 grams, of chitosan are applied per acre of soil when the dry powder blend is distributed in the soil. Evaporated residue powder is also applied to the seed planting zone of soil such that between about 10 grams about about 1,000 grams, and preferably about 30 grams, chitosan are applied per acre of soil.

Besides application in the seed planting zone of the soil, the aqueous solution, the dry powder blend or the evaporated residue powder can also be applied directly to the plant seed. Application of the aqueous solution to seeds is generally performed by either a metered spraying of the seeds with the aqueous solution or by soaking the seeds in the aqueous solution. Preferably, approximately 12 grams of chitosan are applied to approximately 50 pounds of seeds. If the seeds are soaked in the aqueous solution, the soaking usually extends over a period of up to approximately 24 hours. Soaking of seed initiates imbibation of the soaking solution and germination of the seed. Soaking also causes the seed to become heavy, therefore the most commonly soaked seed is rice because rice seed must sink to the bottom of flooded paddies when planted, and if dry would merely float on the flooded paddies, The micronutrient zinc can be included in all commercially available rice seed preparations.

The dry powder blend or the evaporated residue powder is also applied directly to the seeds by metered spraying. When applied by metered spray, the powder blend must be distributed onto dampened seeds in order for the blend to adhere to the seeds. Another common method for applying the powder blend or evaporated residue powder to seeds is to mix the blend or residue powder with dampened seeds in some sort of tumbling device such as a cement mixer. The application rate for the dry powder blend or the evaporated residue powder preferably distributes approximately 12 grams of chitosan onto approximately 50 pounds of seed. The seeds most commonly used are rice, wheat, barley, oat and sorghum.

The evaporated residue powder requires very little moisture to imbibe into the seed. This is a significant advantage in particularly dry planting areas and seasons. There is also a far greater uniformity of absorption of chitosan and non-phytotoxic acid by the seed from the evaporated residue than from a dry powder blend.

Examples of the practice of the invention and the results obtained are recounted below.

EXAMPLE 1

A 3% aqueous solution of chitosan in acetic acid was applied to rice seed by metered spray such that 12.7 grams of chitosan and 12.7 grams of acetic acid were applied to 50 pounds of seed. The rice seed was then allowed to air-dry, after which it was planted with a grain drill at a rate such that 28 grams of chitosan and 28 grams of acetic acid were applied per acre of soil. 110 pounds of treated seed were applied per acre of soil. The total plot planted with treated seed was 1.42 acres.

A control plot of 1.51 acres was planted with untreated rice seed. The untreated rice seed was obtained from the same source as the treated seed. A batch of untreated seed was divided into two lots, one of which was treated as described above and the other of which was not treated at all. The control plot was also planted at a rate of 110 pounds of seed per acre of soil.

The treatment plot and the control plot were contiguous acreage, and were maintained throughout the growing season in identical fashion to the extent possible by man. Both plots were also maintained in identical fashion and planted with the same crop prior to being planted with rice seed. Both plots were planted with rice seed on the same day in early April of the year.

66 days after planting, three random samplings were taken in the treated plot. The random samplings revealed that there were an average of 59 tillers per linear foot of drill row in the treated plot compared with an average of 46.5 tillers per linear foot of drill row in the control plot.

45 days after the initial sampling, the rice plants were fully mature and ready for harvest. Measurement showed that the plants grown from treated seed were in the range of 42 inches to 45 inches tall. The heights of rice plants grown from untreated seed were between 40 inches and 44 inches. Three random samplings from both the treated and the untreated plots showed an average of 230.5 heads per 10 linear feet of drill row in the treated plot as contrasted with an average of 200.6 heads per 10 feet of linear drill row in the control plot. Both the control plot and the treatment plot were harvested in an identical manner to the extent possible.

A comparison of the harvest data is shown below in Table I.

TABLE 1

|  | Total Pounds Harvested | Pounds Per Acre Harvested | Bushels Per Acre Harvested |
|---|---|---|---|
| Treatment Acreage (1.42 acres) | 9,850 | 6,936 | 42.8 |
| Control Acreage (1.51 acres) | 10,150 | 6,721 | 41.4 |

The treated rice seed resulted in a 215 pound per acre increase in rice production, which represented a 3.2% increase in marketable product.

Other observations of the treatment and control acreage showed that the plant foliage color in both plots was comparable, and that there did seem to be more green and immature rice heads on the late tillers of the control acreage as compared to the plants of the treatment acreage.

One possibility for a difference in yield of only 3.2% between the treated acreage and control acreage is that greater plant development of plants from the treated seed drained excess introgen from the finite available quantity, resulting in less-than-adequate amounts of nitrogen being available to the rice plants during panicle filling. It is theorized that additional nitrogen, applied at a rate of about 20 pounds of nitrogen per acre during panicle initiation, would result in a greater yield proportional to the greater head count and its corresponding potential.

EXAMPLE 2

2,500 pounds of wheat seed, which had previously been treated with pentachloronitrobenzene for protection against smuts, damping-off and seed rot, were sprayed with a 2% aqueous solution of chitosan in glutamic acid such that 11.2 grams of chitosan and 1.2 grams of glutamic acid were applied per 50 pounds of seed.

On October 18, two days after the seed treatment, 8.5 acres of an 84.2-acre plot were planted with the treated seed. The remaining 75.7 acres of the plot served as the control, and were planted with untreated wheat seed from the same initial batch as the seed which was treated with the aqueous solution of chitosan.

The treated seed as well as the untreated seed were planted using a Great Lakes 15-foot grain drill. The spacing between rows was 7 inches and the planting depth was ¾ inch to 1¼ inches below the soil surface. The seeding rate was 125 pounds of seed per acre.

The entire 84.2-acre field had been chiseled and disced to prepare the seed bed and the field was "bedded" on five foot centers. Ditches between the beds allowed water to drain from the field during winter rains. During the previous growing season, the field was planted with wheat, which was harvested in late June and the straw burned. Aqua ammonia was shanked into the seed-bed to a depth of 4–5 inches at 100 pounds of nitrogen per acre four days prior to seeding. Additionally, 11-46-0 fertilizer was side-dressed through the drill at a rate of 80 pounds per acre as a starter fertilizer, and to meet the crop's need for phosphorus. The 11-46-0 representation in the fertilizer refers to the respective ratios present of nitrogen to phosphorus to potassium. After planting, all 84.2 acres were maintained in an identical fashion to the extent possible by man.

Sixty-three days after planting, the number of plants in the treatment acreage was compared to the number of plants in the control acreage. Time samplings showed an average of 122.6 plants per 10 linear feet of drill row in the treatment acreage compared to an average of 124.4 plants per 10 linear feet of drill row in the control acreage. These figures represent 1.4% less plant production in the treatment acreage as compared to the control acreage.

Tiller counts were conducted 59 days after planting. Five samplings from the treatment acreage and five samplings from the control acreage showed an average of 315 tillers per 10 linear feet of drill roll in the treatment acreage, as compared to 240 tillers per 10 linear feet of drill row in the control acreage. These figures represent 31.2% greater tillering in the wheat plants grown from treated seed as compared to those wheat plants grown from untreated seed.

A comparison of head counts taken 152 days after planting and 183 days after planting is given below in Tables 2 and 3, respectively.

TABLE II

|  | Days After Planting | Number of Samples Taken | Average Number of Heads per 10 Linear Feet of Drill Row |
|---|---|---|---|
| Treatment Acreage (8.5 acres) | 152 | 7 | 348 |
| Control Acreage (75.7 acres) | 152 | 7 | 270 |

The numbers in Table II above represent a 28.9% greater heading by the wheat plants grown from treated seed as compared to those wheat plants grown from untreated seed.

TABLE III

| | Days After Planting | Number of Samples Taken | Average Number of Heads per 10 Linear Feet of Drill Row |
|---|---|---|---|
| Treatment Acreage (8.5 acres) | 183 | 7 | 300 |
| Control Acreage (75.7 acres) | 183 | 7 | 196 |

The numbers in Table III above represent a 53.1% greater heading by the wheat plants grown from treated seed as compared to those wheat plants grown from untreated seed.

The 8.5 acres of the treatment acreage and 75.7 acres of the control acreage were harvested in an identical manner 251 days after planting. The treatment acreage yielded an average of 2.76 pounds of wheats per acre compared to an average yield of 2,048 pounds of wheat per acre from the control plot. These numbers represent a 34.1% greater yield from the treatment acreage.

The above Examples demonstrate the effectiveness and excellent results obtainable when an aqueous solution of chitosan in glutamic acid is applied directly to seeds. Similarly good results can be expected when the aqueous solution of chitosan in glutamic acid is applied in the seed planting zone either prior to, simultaneously with, or after the planting of the seed. Similar results can also be expected from application of a dry blend of chitosan and glutamic acid to dampened seeds or in the seed planting zone of the soil.

In addition to the rice and wheat of Examples I and II, the aqueous solution or dry powder blend of chitosan and non-phytotoxic acid may be used to influence growth in all food plants, seed plants, fiber plants, fruit plants, nut plants and ornamental plants. Particular seed plants besides rice and wheat include barley, oat and sorghum.

While the invention has been disclosed by reference to the details of preferred embodiments, the disclosure is intended in an illustrative rather than in a limiting sense, as it is contemplated that modifications will readily occur to those skilled in the art, within the spirit of the invention and the scope of the appended claims.

What is claimed is:

1. A process for regulating plant growth comprising:
dissolving chitosan in glutamic acid to produce an aqueous solution comprising 0.1% by volume to 10% by volume chitosan and 0.1% by volume to 10% by volume of glutamic acid, and
distributing said aqueous solution in soil in which plants will be grown, in the seed planting zone.

2. The process of claim 1 wherein said chitosan comprises 2% by volume of said aqueous solution.

3. The process of claim 1 wherein chitosan comprises 2% by volume of the aqueous solution and glutamic acid comprises 2% by weight of the aqueous solution.

4. The process of claim 1 wherein said aqueous solution is distributed in the soil such that between approximately 10 grams of chitosan and approximately 1,000 grams of chitosan are applied per acre of soil.

5. The process of claim 4 wherein approximately 30 grams of chitosan and 30 grams of glutamic acid are applied per acre of soil.

6. The process of claim 4 wherein approximately 30 grams of chitosan are applied per acre of soil.

7. A process for regulating plant growth comprising:
dissolving chitosan in glutamic acid to produce an aqueous solution comprising 0.1% by volume of 10% by volume chitosan and 0.1% by volume to 10% by volume of glutamic acid, and
applying said aqueous solution to plant seeds.

8. The process of claim 7 wherein said chitosan comprises 2% by volume of said aqueous solution.

9. The process of claim 7 wherein said aqueous solution is applied to the plant seeds by a metered spray.

10. The process of claim 7 wherein approximately 12 grams of chitosan are applied to approximately 50 pounds of plant seed.

11. The process of claim 7 wherein said plant seeds may be chosen from the group consisting of rice, wheat, barley, oat and sorghum.

12. The process of claim 7 wherein said aqueous solution is applied to said plant seeds by soaking the plants seeds in the solution for up to approximately 24 hours.

13. The process of claim 7 wherein approximately 12 grams of chitosan and approximately 12 grams of glutamic acid are applied per 50 pounds of plant seed.

14. The process of claim 7 wherein chitosan comprises 2% by volume of the aqueous solution and glutamic acid comprises 2% by weight of the aqueous solution.

15. A process for regulating plant growth comprising:
grinding dry chitosan to powder form with an average particle diameter between about 0.5 μm and 100 μm,
blending said ground form of chitosan with a dry form of glutamic acid with an average particle diameter between about 0.5 μm and 100 μm, such that the weight ratio of chitosan glutamic acid is between about 1:10 and 10:1, and
distributing the blend in soil in which plants will be grown, in the seed planting zone.

16. The process of claim 15 wherein the ground chitosan has an average particle diameter between about 10 μm and 30 μm, and the glutamic acid has an average particle diameter between about 10 μm and 30 μm.

17. The process of claim 16 wherein the weight ratio of chitosan to glutamic acid is about 1:1.

18. The process of claim 15 wherein said blend of chitosan and glutamic acid is distributed in the soil such that between approximately 10 grams of chitosan and approximately 1,000 grams of chitosan are applied per acre.

19. The process of claim 18 wherein approximately 30 grams of chitosan is applied per acre of soil.

20. A process for regulating plant growth comprising:
grinding dry chitosan to powder form with an average particle diameter between about 0.5 μm and 100 μm;
blending said ground form of chitosan with a dry form of glutamic acid with an average particle diameter between about 0.5 μm and 100 μm, such that the weight ratio of chitosan to glutamic acid is between about 1:10 and 10:1, and
applying the blend to dampened plant seeds.

21. The process of claim 20 wherein the ground chitosan has an average particle diameter between about 10 μm and 30 μm, and the glutamic acid has an average particle diameter between about 10 μm and 30 μm.

22. The process of claim 20 wherein said blend is applied to the dampened plant seeds by metered spray.

23. The process of claim 20 wherein said blend is applied to the dampened seeds by mixing the blend and the dampened seeds in a tumbling device.

24. The process of claim 20 wherein approximately 12 grams of chitosan are applied to approximately 50 pounds of plant seed.

25. The process of claim 20 wherein said plant seeds may be chosen from the group consisting of rice, wheat, barley, oat and sorghum.

26. A process for regulating plant growth comprising applying a ground powder with an average particle diameter between about 10 μm and about 30 μm obtained from the residue of an evaporated, concentrated aqueous solution comprising about 3% by volume or greater of chitosan and about 3% by volume or greater of glutamic acid in the soil in which plants will be grown, in the seed planting zone.

27. The process of claim 26 wherein chitosan and glutamic acid are present in equal volume percentages.

28. The process of claim 26 wherein the ground powder is applied to the soil such that between approximately 10 grams of chitosan and approximately 1,000 grams of chitosan are applied per acre.

29. The process of claim 28 wherein approxiamtely 30 grams of chitosan are applied per acre.

30. A process for regulating plant growth comprising applying a ground powder with an average particle diameter between about 10 μm and about 30 μm obtained from the residue of an evaporated, concentrated aqueous solution comprising about 3% by volume or greater of chitosan and about 3% by volume or greater of glutamic acid to dampened plant seeds.

31. The process of claim 30 wherein chitosan and glutamic acid are present in equal volume percentages.

32. The process of claim 30 wherein the ground powder is applied to dampened seeds by metered spray.

33. The process of claim 30 wherein the ground powder is applied to dampened seeds by mixing the powder and the dampened seeds in a tumbling device.

34. The process of claim 30 wherein approximately 12 grams of chitosan are applied to approximately 50 pounds of seed.

35. A plant growth regulating composition comprising an aqueous solution comprising between about 0.1% by volume and about 10% by volume chitosan and between about 0.1% by volume and about 10% by volume of glutamic acid.

36. The plant growth regulating composition of claim 35 wherein chitosan comprises about 2% of said aqueous solution and glutamic acid comprises about 2% of said aqueous solution.

37. A plant growth regulating composition comprising a blend of chitosan in powder form and glutamic acid in powder form, and chitosan and glutamic acid being in a weight ratio of between about 1:10 and about 10:1.

38. The plant growth regulating composition of claim 37 wherein chitosan and glutamic acid are present in a weight ratio of about 1:1.

39. The plant growth regulating composition of claim 37 wherein the average particle diameter of chitosan is between about 0.5 μm and about 100 μm and the average particle diameter of glutamic acid is between about 0.5 μm and about 100 μm.

40. The plant growth regulating composition of claim 39 wherein the average particle diameter of chitosan is between about 10 μm and about 30 μm.

41. A plant growth regulating composition comprising the ground residue from the evaporation of a concentrated aqueous solution comprising 3% by volume or greater of chitosan and 3% by volume or greater of glutamic acid.

42. The Plant growth regulating composition of claim 41 wherein chitosan and glutamic acid are present in equal volume percentages.

43. The plant growth regulating composition of claim 41 in which the average particle diameter of the ground residue is between about 10 μm and about 30 μm.

* * * * *